United States Patent [19]
Rafft et al.

[11] Patent Number: 4,737,361
[45] Date of Patent: Apr. 12, 1988

[54] ALPHA ADRENERGIC AMINE OF SUBSTANTIAL ALPHA$_2$ ADRENERGIC AMINE ACTIVITY AS AN ANTIPERSPIRANT

[75] Inventors: Ronald R. Rafft, Towaco; Michael D. Helman, Edison, both of N.J.

[73] Assignee: Bristol-Myers Company, New York, N.Y.

[21] Appl. No.: 871,652

[22] Filed: Jun. 6, 1986

[51] Int. Cl.$^4$ .......................... A61K 7/32; A61K 9/12
[52] U.S. Cl. ................ 424/65; 424/DIG. 5; 424/47; 424/69; 514/938
[58] Field of Search ............................................ 424/65

[56] References Cited

U.S. PATENT DOCUMENTS 3,312,709  4/1967  Kilmer ................................. 424/65
3,326,768  6/1967  Kilmer et al. ........................ 424/65
3,624,200 11/1971  Moffett ................................ 424/65

OTHER PUBLICATIONS

American Hospital Formulary Service, 1965, vol. 2, 12:12, 52:24 and 52:32.

Primary Examiner—Dale R. Ore
Attorney, Agent, or Firm—Charles J. Zeller; Morton S. Simon

[57] ABSTRACT

An antiperspirant process and composition wherein the active antiperspirant ingredient is an alpha adrenergic amine that has at least a substantial alpha$_2$ adrenergic amine activity component.

9 Claims, No Drawings

ALPHA ADRENERGIC AMINE OF SUBSTANTIAL ALPHA$_2$ ADRENERGIC AMINE ACTIVITY AS AN ANTIPERSPIRANT

This invention relates to a process for inhibiting perspiration, and to compositions that are useful for such a process. More particularly, it concerns processes and compositions of the aforesaid character which employ as their principal active ingredient at least one alpha adrenergic amine that has at least a substantial alpha$_2$ adrenergic amine activity component. This active ingredient may be comprised of an alpha adrenergic amine which has both alpha$_1$ and alpha$_2$ activity in which the alpha$_2$ activity is substantial or it may be an alpha adrenergic amine which has essentially only alpha$_2$ activity with no or only a minimal amount of alpha$_1$ activity. The process has particular utility in inhibiting axillary or underarm perspiration in a subject.

Adrenergic or sympathomimetic amines constitute a well-known class of drugs which are characterized by the fact that in general their effects resemble the responses due to stimulation of adrenergic nerves. Although this is a convenient way to characterize these amines it does not mean that all the amines within this group act with the same degree of intensity.

The adrenergic or sympathomimetic amines have been further classified on the basis of the receptors with which they can interact to elicit a response in sympathetic effector cells. On the basis of such considerations the sympathomimetic or adrenergic amines have been classified as alpha and beta adrenergic amines (See Louis S. Goodman and Alfred Gilman; *The Pharmacological Basis of Therapeutics*, 4th Edition, 1970 p. 479–480). Based on similar considerations, the alpha adrenergic amines have been further classified as alpha$_1$ and alpha$_2$ adrenergic amines.

In the real world, however, alpha adrenergic amines are known to exist which have activity that is spread across the whole spectrum of activity between alpha$_1$ and alpha$_2$ adrenergic amines. Thus there are alpha adrenergic amines that exhibit essentially only alpha$_1$ activity with no or only insignificant alpha$_2$ activity. Similarly there are also alpha adrenergic amines whose activity is essentially only of the alpha$_2$ type with no or only insignificant alpha$_1$ activity. Between these two extremes, there exists alpha adrenergic amines of the mixed type that have varying degrees of alpha$_1$ and alpha$_2$ activity. The alpha adrenergic amines that have been found to be effective for the purposes of the present invention are those that are essentially of the "pure" alpha$_2$ type or of the mixed type which have a substantial alpha$_2$ activity component. Those mixed alpha adrenergic amines that have alpha$_2$ components that are closest to the essentially pure alpha$_2$ adrenergic amines are expected to be the most effective.

Although there are other modes of applying the compositions used to practice the present invention it is generally visualized that it will be practiced by topically applying an effective antiperspirant amount of the present composition to the skin of the subject and particularly those areas of the skin where sweating is likely to be the most intense, as for example the axilla of the subject. Furthermore, the composition may be applied in a variety of dosage forms such as for example, creams, lotions, sprays, sticks, powders, solutions, gels, transdermal patches, suspensions, emulsions, aerosol compositions, etc.

It is known in the prior art that certain adrenergic amines stimulate perspiration in certain animals. Thus, for example, J. Bijman et al, studied the control of sweating in single equine sweat glands (Am. J. Physiol (United States) March 1984, 246 p. 349–53). They reported that moderate sweating responses were obtained with the alpha-adrenergic agonists phenylephrine and methoxamine. Similarly, K. G. Johnson et al, studied sweating in intact or isolated perfused ox skin (Comp. Biochem. Physiol [c](England) 1982, 73(2) p. 265–270). They also report that in the isolated perfused skin, alpha adrenergic drugs induced sweating. A somewhat related study was conducted by K. Sato who studied the response of isolated cannulated single monkey palm eccrine sweat glands to, among other things, alpha and beta adrenergic agents (Am. J. Physiol, Jan 1981, 240(1) p. 44–51). He reports that all these agents stimulate sweating, but to a different degree, the least stimulation being noted with the alpha adrenergic agonists. He concluded that the isolated eccrine sweat glands retain their pharmacologic viability in vitro and show responsiveness to cholenergic as well as alpha and beta adrenergic stimulation.

In light of the above teachings it was indeed unexpected that the alpha adrenergic amines with at least a substantial alpha$_2$ adrenergic amine activity component would be effective in inhibiting perspiration in a subject.

The alpha adrenergic amines that are useful in the practice of the present invention are varied. As indicated above what is essential is that they have at least a substantial alpha$_2$ adrenergic amine activity component. A number of alpha adrenergic amines are known in this art which have these characteristics. By way of example mention may be made of xylometazoline, oxymetazoline, naphazoline, etc.. These may be used in the form of their pure bases but more generally they will be used as acid addition salts which can be tolerated by the skin e.g. hydrochloride.

The compositions that are useful in the practice of the present invention will contain the adrenergic amine, as further defined herein, at an effective concentration level at which it may serve to inhibit perspiration. This will vary somewhat over a range depending upon the vehicle in which it is contained or the degree of antiperspirant activity that is desired. Generally, however, it will be present at a concentration level ranging from about 0.1 to about 20% by weight based on the total weight of the composition with the preferred range being from about 2% to about 12% on the same weight basis, with the most suitable range being from about 4% to about 10% on the same weight basis.

In practicing the process of this invention the products are applied to the axilla or underarm of the subject to cover the axillary vault with a coating of the composition. This will usually involve a few strokes of the applicator loaded with product to the underarm or in the case of an aerosol product one or a few sprays of the aerosol product to the axillary vault. All that is required is that enough be applied to cover the axillary vault and thereby inhibit axillary perspiration.

As indicated above, the products that are useful for the purposes of this invention may take any of a variety of dosage forms. It may constitute a simple solution, suspension or emulsion of the active ingredient or ingredients in a suitable solvent or other liquid vehicle. Other adjuvants may be added to such a solution, suspension or emulsion to help solubilize or stabilize the active ingredient or to facilitate the penetration of the active ingredients into the axillary skin and particularly to the axilla of a subject.

Where the active ingredients are to be incorporated in a cream or lotion the finished product will ordinarily contain other ingredients commonly used in formulating such creams or lotion products. Thus, such materials as emulsifying agents, suspending agents, humectants, emollients, solvents, coloring agents, perfumes, opacifying agents, buffers, stabilizers, masking agents, preservatives, anti-oxidants, sequestrants, etc. will be contained in such compositions. By way of further specifically illustrating the vehicle components of, for example, a roll-on antiperspiration formulation that may be employed along with the active antiperspirant ingredients described above in accordance with the present invention the following may be mentioned:

Emulsifying/Suspending Agents: magnesium aluminum silicate, glyceryl stearate, quaternium-18 hectorite, Laureth-23, Laureth-4, Cetyl alcohol, Steareth-2, PPG-11 stearyl ether, Steareth-20, PPG-15 stearyl ether, Lapyrium chloride, Lauric acid, Polysorbate-20, Stearyl alcohol, PEG-40 stearate, Lanolin alcohol, PEG-100 stearate, Hydrogenated castor oil, PEG-50 stearate, Steareth-20, PEG-2 stearate, PPG-5 lanolin ether, Ceteth-2, Ceteth-20, Ceteareth-20, Glycol stearate, PEG-4 oleate, PEG-75 lanolin oil, PEG-75 stearate, PEG-8 laurate, and PEG-100 stearate.

Emollients: Cyclomethicone, PPG-14 butyl ether, Propylene carbonate, Simethicone, Laneth-10 acetate, Mineral oil, Isopropyl myristate, Lauryl lactate, Dimethicone, Isodecyl oleate, Isopropyl isostearate, Isopropyl lanolate, Eicosanol, Isopropyl palmitate, and Oleyl alcohol.

Humectants: Glycerin and Propylene glycol.

Miscellaneous: Water, SD alcohol 40, Aluminum starch octenyl succinate, Silica, Polyethylene, Glycine, Talc, Paraffin and Titanium dioxide.

Preservatives/Antioxidants/Sequestrants: EDTA, Methlyparaben, Propylparaben, BHT, Trisodium HEDTA, Butylparaben, Formaldehyde soln., Ascorbic acid and Sorbic acid.

When incorporated in a stick, the active ingredients of this invention may be distributed in a mixture of waxes that constitute the back-bone of these sticks. In addition, such products may also contain other ingredients that go to rendering the stick organoleptically acceptable or to ease the application of the product to the axillary vault, e.g. gellants, emollients, filler, etc. To illustrate, more particularly, the vehicle components that may be present in an antiperspirant stick formulation along with the active antiperspirant ingredients described above in practicing this invention, the following may be given:

Gellants: Stearyl alcohol, Hydrogenated castor oil, PEG-8 distearate, Glyceryl stearate, PEG-100 stearate, Paraffin, Steareth-100, C-20 alcohol, Ozokerite, Stearamide MEA, Stearic acid and Synthetic wax.

Emollients: Cyclomethicone, PPG-14 butyl ether, Eicosanol, Dipropylene glycol, Lauryl lactate, PPG-3 myristyl ether and Simethicone.

Other additives: talc.

In preparing an aerosol product in accordance with this invention the ingredients commonly found in aerosol antiperspirant products will be utilized. These will include such material as propellants, solvents, emollients, preservatives, sequestrants, etc.. The alpha adrenergic amines will be distributed in any suitable fashion in these aerosol products.

It is sometimes advantageous to add to the compositions employed in this invention materials which will enhance the penetration of the antiperspirant actives essential to the practice the instant invention into or through the skin. A number of materials are available which may be used for this purpose. By way of example mention may be made of the following: oleate esters of sorbitol, octyl palmitate, ETOH, polyoxamers. When such enhancers are employed they may be used over a wide range of concentrations. Usually this may be in the range of from about 1% to about 99% by weight based on the total weight of the composition with the preferred range being from about 25% to about 75% of the same weight basis.

The mechanism for the antiperspirant action of the adrenergic amines employed in this invention is unknown. Applicant can only speculate that it may be due to smooth muscle constriction associated with the sweat glands. Alternatively, a presynaptic pathway may be involved. However, what is known is that in the test method employed, inhibition of perspiration has been demonstrated and that this inhibition is dose related.

The following examples are given to further illustrate this invention. It is to be understood, however, that the invention is not limited thereto.

The chemical definition for the materials that are identified by trade names in the examples are given below. The nomenclature for these materials is generally the nomenclature adopted in the CTFA Cosmetic Ingredient Dictionary, third edition:
1. Bentone 38: Quaternium-18 Hectorite
2. CAB-0-Sil M5: Silica
3. FT-300 Wax: High melting paraffin wax
4. Fluid AP: PPG-14 Butyl Ether
5. Ionol CP: BHT
6. Witconol APS: PPG-11 Stearyl Ether
7. Brij 72: STEARETH-2
8. Brij 78: STEARETH-20

| ANTIPERSPIRANT SUSPENSION ROLL-ON PRODUCTS | | |
|---|---|---|
| INGREDIENT | % W/W Example 1 BY3445-56A | % W/W Example 2 BY3445-56B |
| Bentone 38 | 1.75 | 1.75 |
| Propylene Carbonate | 0.60 | 0.60 |
| Cyclomethicone 7158 | 87.40 | 87.40 |
| Dipropylene Glycol | 0.05 | 0.05 |
| CAB-O-SIL M5 | 0.20 | 0.20 |
| Dimethicone 350 cs. | 5.00 | 5.00 |
| Naphazoline HCl | 5.00 | — |
| Oxymetazoline HCl | — | 5.00 |
| | 100.00 | 100.00 |

PROCEDURE:
Combine all ingredients except active in a Waring Blender. Mix 10 minutes at high speed. Mix slowly with Lighting agitator while cooling to 90° F. Increase mixing and add active. Mix 5 minutes.

| ANTIPERSPIRANT SUSPENSION STICK PRODUCTS | | |
|---|---|---|
| INGREDIENT | % W/W Example 3 BY3445-55A | % W/W Example 4 BY3445-55B |
| Stearyl Alcohol | 13.20 | 13.20 |
| Castorwax MP-80 | 7.90 | 7.90 |
| FT-300 Wax | 4.00 | 4.00 |
| Fluid AP | 5.30 | 5.30 |
| Ionol CP | 0.50 | 0.05 |
| Cyclomethicone 7158 | 56.65 | 56.65 |

-continued

ANTIPERSPIRANT SUSPENSION STICK PRODUCTS

| INGREDIENT | % W/W Example 3 BY3445-55A | % W/W Example 4 BY3445-55B |
|---|---|---|
| Talc 5251 | 7.90 | 7.90 |
| Naphazoline HCl | 5.00 | — |
| Oxymetazoline HCl | — | 5.00 |
| | 100.00 | 100.00 |

PROCEDURE:
Combine waxes and melt at 220° F. Slowly add the Fluid AP (reheat if necessary). Combine the remaining ingredients and heat to 160° F. Slowly add the wax phase to the cyclomethicone phase and cool to 160° F. Pour into stick molds at 160° F.

ANTIPERSPIRANT EMULSION ROLL-ON PRODUCTS

| INGREDIENT | % W/W Example 5 BY3445-57A | % W/W Example 6 BY3445-57B |
|---|---|---|
| Witconol APS | 3.00 | 3.00 |
| Brij 72 | 1.60 | 1.60 |
| Brij 78 | 1.40 | 1.40 |
| Water | 89.00 | 89.00 |
| Naphazoline HCl | 5.00 | — |
| Oxymetazoline HCl | — | 5.00 |
| | 100.00 | 100.00 |

PROCEDURE:
Heat the Witconol APS and Brijs to 140° F. Heat the water to 140° F. Add the oils to the water and mix with moderate Lighting agitation while cooling to 90° F. Add the active and mix 5-10 minutes.

To test the effectiveness of the adrenergic amines encompassed in this invention in inhibiting perspiration the following tests were carried out.

I. Preparation of Test Solutions

A series of test solutions were prepared by dissolving various quantities of xylometazoline HCl, oxymetazoline HCl and naphazoline HCl in freshly prepared distilled water. In the case of xylometazoline HCl 0.003%, 0.03%, 0.15% and 0.3% solutions were prepared. In the cases for oxymetazoline HCl and naphazoline HCl 0.15% solutions were made. The control material is distilled water.

II. Animal Selection

A. Prior to testing, rats are routinely acclimated to the laboratory environment for seven days and gross observations are made to ensure good health of animals to be tested.
B. Sprague Dawley rats, male and/or female (175-250 gm) are selected for test and identified by cage label and ear tag number.
C. A minimum of 6 animals is used in testing each solution.

III. Test Procedure

A. Test room should be maintained at a temperature of 78°±2° F.
B.
1. Test animals are injected intramuscularly with Innovar Vet ™ (0.01 ml/100 gm body wt.) by use of a 0.25 ml tuberculin syringe with a 26 or 27 gauge needle. Animals are then returned to their cages.
2. 10-15 minutes post injection the animals are placed in a harness and suspended so that their feet do not touch any surfaces.
3. Both hind feet are then swabbed with 70% ethyl alcohol (ETOH) to remove any debris.
4. The four interdigital palmar foot pads on one hind foot are then treated with test material while the opposite hind foot is treated with the control material.
5. After treatment of all animals, an iodine solution (2% in 95% ETOH wt./vol.) is applied to both hind feet.
6. 30 minutes post treatment the hind feet are then painted with a suspension of starch and castor oil (50/50, wt./vol.).
7. 40 minutes post treatment Polaroid photos (3X, using Polaroid Type Film 669) are taken of both hind feet in the same frame.

IV. Determining Antiperspirant Activity

1. The number of activated sweat glands in each of the four palmar foot pads is quantitated by manually counting the black dots observed in the photo of the control and test treated feet.
2. The ratio of the total number of secreting sweat glands on the control foot vs the total number of secreting sweat glands on the test foot is used to estimate the percent inhibition of sweat in the rat foot pad.
3. The following formula is used to calculate activity.

Percent inhibition of sweat in the rat foot pad =

$$\left(1 - \frac{\text{number of sweat glands/test foot}}{\text{number of sweat glands/control foot}}\right) \times 100$$

The results of these tests are summarized in Table I below:

| Test Material | Concentration Tested (%) | Approx. % Inhibition |
|---|---|---|
| Xylometazoline HCl | 0.003 | 30 |
| Xylometazoline HCl | 0.03 | 50 |
| Xylometazoline HCl | 0.15 | 80 |
| Xylometazoline HCl | 0.3 | 88 |
| Oxymetazoline HCl | 0.15 | 92 |
| Naphazoline HCl | 0.15 | 95 |

As will be seen from this data perspiration inhibition has been demonstrated with each of the compositions treated. In addition, as seen from the xylometazoline HCl studies, the percent inhibition increased with the increase in concentration of the test drug i.e. a dose response has been demonstrated.

What is claimed is:

1. A process for inhibiting perspiration in a subject which comprises applying to the axilla of said subject a composition containing an antiperspirant effective amount of an alpha adrenergic amine that has at least a substantial alpha$_2$ adrenergic amine activity component.

2. A process according to claim 1 wherein the alpha adrenergic amine is an essentially pure alpha$_2$ adrenergic amine.

3. A process according to claim 1 wherein the alpha adrenergic amine is a mixed alpha$_1$ and alpha$_2$ adrenergic amine.

4. A process according to claim 1 wherein the alpha adrenergic amine is selected from the group consisting of xylometazoline, oxymetazoline, naphazoline, their pharmaceutically acceptable salts and mixtures thereof.

5. A process according to claim 1, 2, 3 or 4 wherein said alpha adrenergic amine is present in said composition at a concentration in the range of from about 0.1% to about 20% by weight based on the total weight of said composition.

6. A process according to claim 1, 2, 3 or 4 wherein said alpha adrenergic amine is present in said composition at a concentration in the range of from about 2% to about 12% by weight based on the total weight of said composition.

7. A process according to claims 1, 2, 3, or 4 wherein said area of skin is the axilla of said subject.

8. A process according to claims 1, 2, 3 or 4 wherein said area of skin is the axilla of said subject and said alpha adrenergic amine is present in said composition at a concentration in the range of from about 0.1% to about 20% by weight based on the total weight of said compoition.

9. A process according to claims 1, 2, 3 or 4 wherein said area of skin is the axilla of said subject and said alpha adrenergic amine is present in said composition at a concentration in the range of from about 2% to about 12% by weight based on the total weight of said composition.

* * * * *